United States Patent [19]
Horvath

[11] 4,010,495
[45] Mar. 8, 1977

[54] ARTIFICIAL WRIST AND ARM PROSTHESIS

[75] Inventor: Eduard Horvath, Vienna, Austria

[73] Assignee: Otto Boch Orthopadische Industries KG, Duderstadt, Germany

[22] Filed: May 15, 1974

[21] Appl. No.: 470,080

[30] Foreign Application Priority Data

May 17, 1973 Austria .............. 4334/73

[52] U.S. Cl. ................................. 3/12.4
[51] Int. Cl.² ......................... A61F 1/06
[58] Field of Search ............... 3/12–12.8, 3/21

[56] References Cited

UNITED STATES PATENTS

| 2,457,316 | 12/1948 | Northrop et al. ............ 3/12.5 |
| 2,669,727 | 2/1954 | Opuszenski ................. 3/12.7 |

FOREIGN PATENTS OR APPLICATIONS

| 155,917 | 12/1920 | United Kingdom .......... 3/21 |
| 161,615 | 12/1957 | Sweden .................... 3/12.8 |

OTHER PUBLICATIONS

Orthopaedic Appliances Atlas, vol. 2, (Artificial Limbs) by J. W. Edwards – Ann Arbor, Mich. 1960, pp. 40 and 147.

*Primary Examiner*—Ronald L. Frinks
*Attorney, Agent, or Firm*—Karl F. Ross; Herbert Dubno

[57] ABSTRACT

The artificial wrist serves to connect an arm prosthesis shaft to an implement and comprises distal retaining means, a proximal retaining member adapted to extend into said prosthesis shaft and formed with first and second engaging surfaces, locking means interlocking with said distal retaining means and said first engaging surface to hold said distal retaining means and said proximal retaining member axially together, a sliding surface bearing adapted to rotatably connect an implement to said distal retaining means, and rotatable coupling means which engage said second engaging surface and are adapted to engage said prothesis shaft.

52 Claims, 8 Drawing Figures

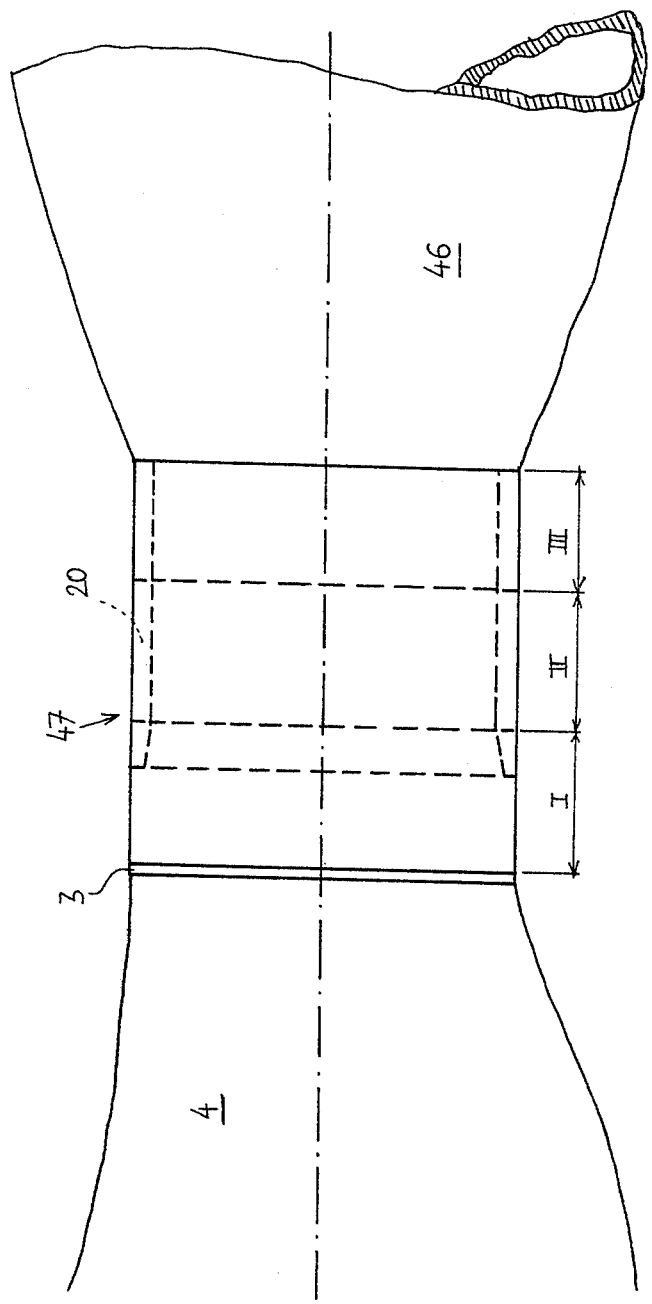

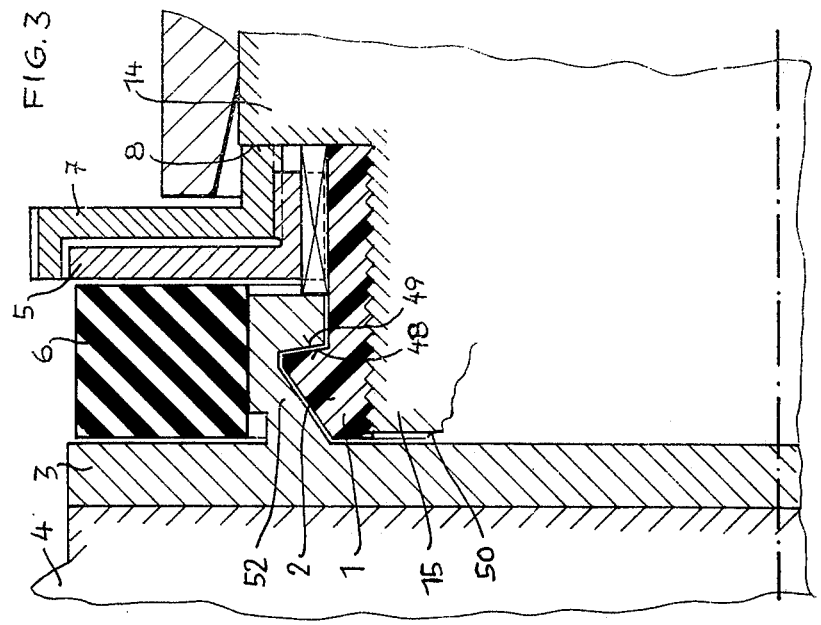
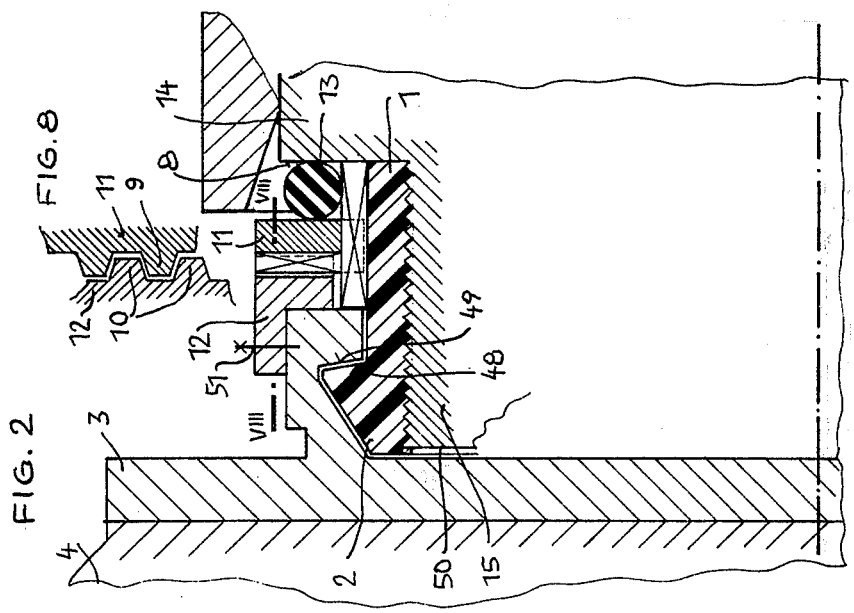

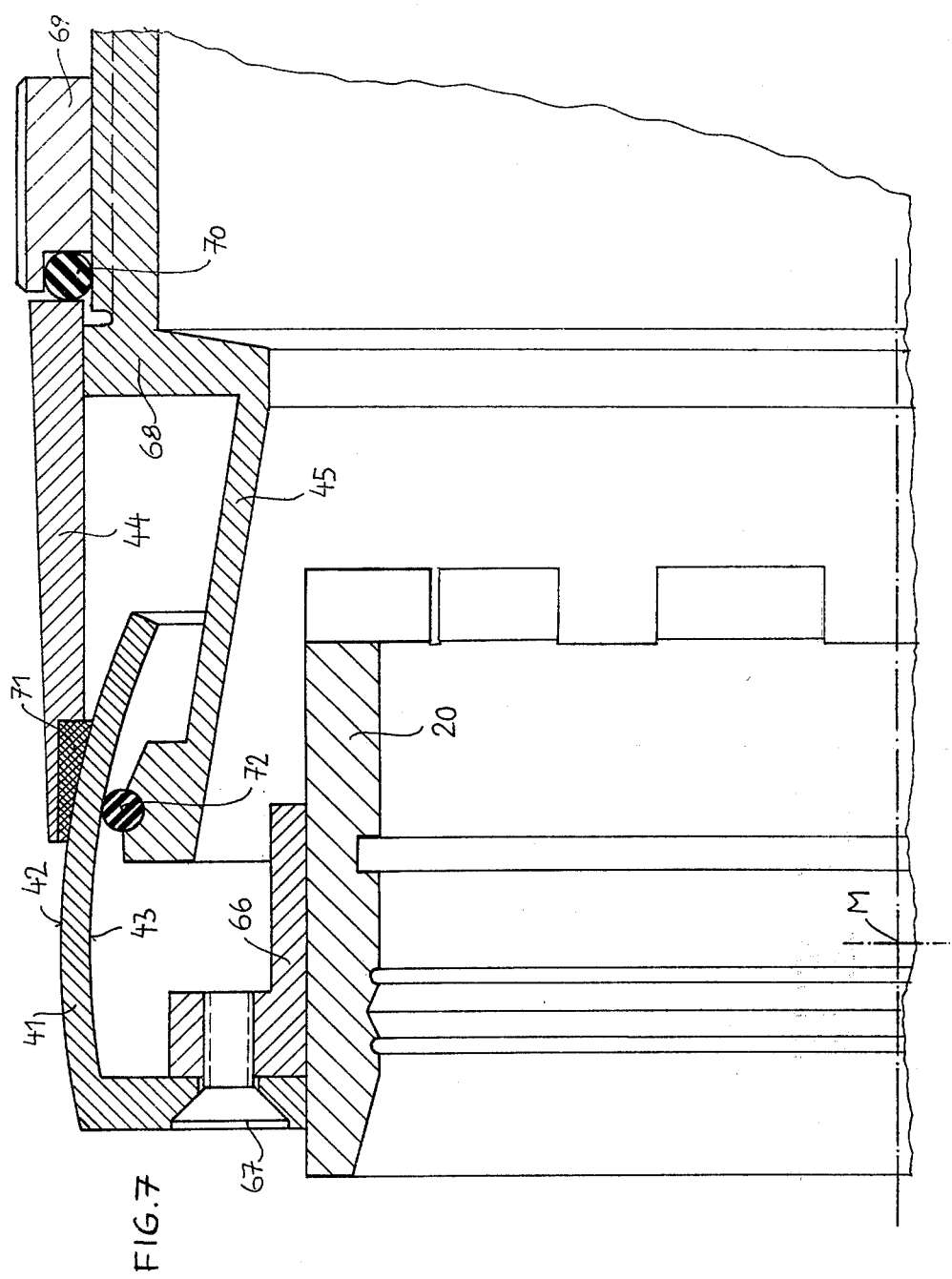

ARTIFICIAL WRIST AND ARM PROSTHESIS

This invention relates to an artificial wrist for arm prostheses which comprise a prosthesis shaft and an artificial hand, which is connected to the prosthesis shaft and consists, if desired, of an implement.

It is an object of the invention to provide a wrist which has a minimum of standardized parts, and which can perform all functions which are desired in a given case.

This object is accomplished according to the invention by the provision of a sliding surface bearing, which is disposed adjacent to the carpus of the artificial hand and enables a passive rotation of the hand, retaining means which serve to establish a connection to the prosthesis shaft and comprise a rolling element bearing, such as a ball bearing, or a bushing, and a retaining member which is disposed at the hand end of the prosthesis shaft and is provided with tracks for the rolling elements of the rolling element bearing or for engaging the bushing and with supporting faces for supporting rotary coupling means provided between the end of the prosthesis shaft and the rolling element bearing or other locking means.

The wrist according to the invention is thus divided into three zones. The first zone contains those elements which permit of a passive movement of the artificial hand relative to the prosthesis shaft so that the gripping tools, such as fingers, can be moved to the desired position. The second zone contains the so-called retaining means, which comprise those parts which enable a detachable connection of the artificial hand to the prosthesis shaft so that one artificial hand can be replaced by another or by an implement. The third zone contains the coupling means, i.e., those elements which permit of a connection to drive means for rotating the artificial hand or which non-rotatably connect the artificial hand to the prosthesis shaft. Because various designs may be adopted for the zones, the wrist can perform a large number of functions.

For instance, in a preferred embodiment of the invention the sliding surface bearing may be provided with friction or detent elements so that the artificial hand can be adjusted continuously or in steps relative to the shaft of the prosthesis.

In a preferred embodiment of the wrist according to the invention, the second zone may be designed so that the rolling elements, such as balls, of the rolling element bearing which serves to connect the artificial hand to the prosthesis shaft, or other locking means, are adapted to be movable by an adjusting mechanism in a substantially radial direction into and out of engagement with a track, which is formed, e.g., by two axially spaced apart wire rings, the track is provided on a retaining member connected to the prosthesis shaft or to the artificial hand, and the rolling elements or other locking means are provided on a retaining member connected to the prosthesis shaft or to the artificial hand, and the rolling elements or other locking means are provided on a retaining member connected to the artificial hand or to the prosthesis shaft. In that embodiment, a simple radial adjustment of the rolling elements or a radial expansion of the locking means will enable a connection to be established between the prothesis shaft and the artificial hand.

According to a further feature of the invention the mechanism for adjusting the rolling elements, particularly the balls, may comprise a retaining ring, which is displaceable in the axial direction of the rolling element bearing and which in that position in which, the rolling elements positively connect the prosthesis shaft to the artificial hand, forms a raceway for the rolling elements. In that embodiment one element of the adjusting mechanism forms also a raceway for the rolling elements. According to an additional feature of the invention, the retaining ring for the rolling elements is fitted on that retaining member which is connected to the artificial hand and which is screw-threaded in the sleeve which forms the sliding surface bearing and is provided with bores which enable an axial displacement of the retaining ring and extend at an acute angle of, e.g., 30°, to the axis of the sleeve and cooperate with pins, which are slidably guided in said bores and at one end engage the retaining ring and at the other end are supported on a bushing, which is axially slidably mounted in a bore of the retaining member, whereby an axial displacement of the retaining ring is enabled. The axial displacement required to separate the joint may be accomplished in various ways. It is preferable to provide for a separation of the joint by a passive movement of the artificial hand. In this connection it is a feature of the invention that the bushing which is axially displaceably mounted in the retaining member is non-rotatably connected to the retaining member, which is connected to the artificial hand, said non-rotatable connection is provided, e.g., by means of a pin, which engages a groove formed in the retaining member, and the bushing is provided with an axially protruding cam on that end face which faces the artificial hand and which cooperates with a second cam, which is preferably similarly shaped and which is firmly connected to the artificial hand, particularly to the carrying plate thereof. In that arrangement, a predetermined passive rotational movement of the artificial hand causes the second cam to engage the cam which axially protrudes from the end face of the axially displaceable bushing, and a continued rotation of the artificial hand causes the cams to slide one on the other so that the bushing is axially displaced and the joint between the prosthesis shaft and the artificial hand is separated.

Whereas a rolling element bearing may be used as locking means for connecting the prosthesis shaft to the artificial hand, these locking means may be simplified by the use of a bushing, which is slit throughout its length and is formed on its outside peripheral surface with two shoulders, which are spaced apart by the same distance as the wire rings, and an expanding mandrel is provided, which serves to expand the bushing and which, if desired, is adapted to be inserted into the bushing in the axial direction thereof and then slides on a conical inside surface of the bushing.

Another embodiment of the invention is characterized in that the retaining member which is connected to the artificial hand and which carries the rolling elements, such as balls, or the bushing serving as locking means for connecting the prosthesis shaft to the artificial hand, interengages with a coupling member which is mounted in the retaining member that is connected to the prosthesis shaft. That coupling member may be rotatably or non-rotatably mounted in the retaining member that is connected to the prosthesis shaft and in dependence thereon provides for a non-rotatable connection between the rolling element bearing or other locking means and the end of the prosthesis shaft or enables a transmission of a rotational movement from other rotary means, such as an arm stump, an electric motor, a pneumatic or hydraulic fluid drive, by means of the rolling element bearing or other locking means to the artificial hand.

According to another embodiment of the invention, the prosthesis shaft or the retaining member connected thereto is connected to a spherical shell, which has a center disposed inside said retaining member or the prosthesis shaft, and two clamping rings are provided, which respectively engage the outside and inside surfaces of the spherical shell and which are axially displaceable relative to each other in the direction of their axis and one of which is firmly connected to the prosthesis shaft or the retaining member connected thereto. Such wrist enables a movement of the artificial hand to any desired angular position relative to the axis of the prosthesis shaft.

Finally, it is a feature of the invention that the hand end portion of the prosthesis shaft and all elements incorporated in said portion may be so small that they can be accommodated within the smallest periphery which can accommodate the hand whereas an adaptation to hand peripheries which have a larger extent and different configuration may be provided for by an application of thermoplastic or thermosetting plastic material or of additional annular members, particularly of metal, in the desired configuration.

The invention will now be explained more fully and by way of example with reference to the drawing, in which FIG. 1 is a diagrammatic view showing a wrist designed according to the invention and disposed between a prosthesis shaft and an artificial hand or an implement.

FIG. 2 is a longitudinal sectional view showing an embodiment of the elements which enable a passive movement of the artificial hand relative to the prosthesis shaft.

FIG. 3 shows a modification of the elements shown in FIG. 2 and enabling a passive movement of the artificial hand.

FIG. 7 is a longitudinal sectional view showing a ball-type joint provided on the prosthesis shaft and FIG. 8 is a sectional view taken on line VIII—VIII in FIG. 2, developed onto a straight line.

Figure 4:
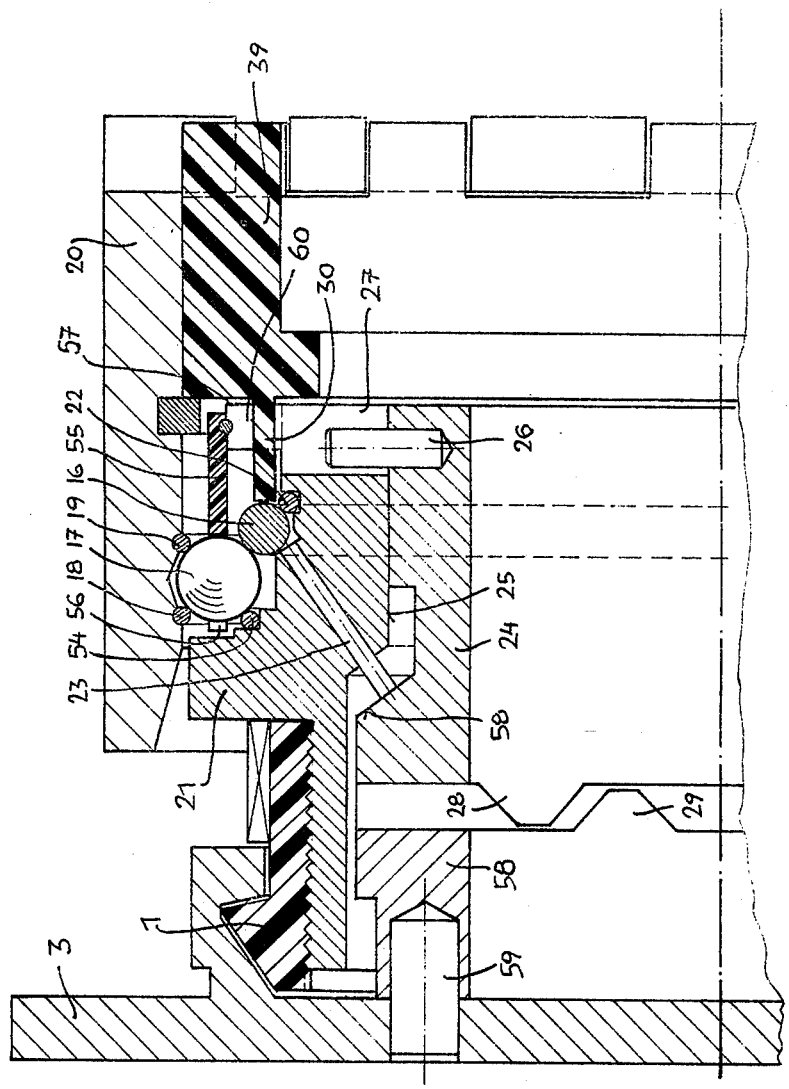
FIG. 4 is a longitudinal sectional view showing the means for retaining the artificial hand on the prosthesis shaft.

FIG. 1 shows an artificial hand 4, which by an artificial wrist generally designated 47 is connected to a prosthesis shaft 46. Only the hand end portion of said shaft is shown on the drawing. The artificial wrist 47 is composed of elements which may be considered as being disposed in three zones, I, II, and III. Zone I contains those elements which permit of a passive movement of the artificial hand 4 relative to the prosthesis shaft 46 so that the artificial hand 4 or an implement used instead of the artificial hand may be moved to a position which is required for a desired function. The second zone II contains the retaining means, which enable a detachable connection to be established between the artificial hand 4 and the prosthesis shaft 46.

Zone III contains the coupling means, which either permit of connecting the artificial hand to means for rotating the same or permit of non-rotatably connecting the artificial hand to the prosthesis shaft.

A sliding surface bearing is provided adjacent to the carpus and permits of a rotation of the artificial hand 4 relative to the prosthesis shaft 46. This sliding surface bearing consists of a sleeve 1, which is hook-shaped in a meridional section. The hook portion 2 of the sleeve extends into a correspondingly shaped recess in a carrying plate 3 for the artificial hand 4. The sleeve 1 consists preferably of plastic material and is injection-molded in the recess of the carrying plate. For special applications, which will be discussed hereinafter, the sleeve 1 may be clamped to the carrying plate 3 so that the function of the bearing is eliminated. To clamp the sleeve 1 to the carrying plate 3, the sleeve 1 is axially displaced (to the right in FIGS. 2 and 3) so that the inclined surface 48 of the hook portion 2 of the sleeve 1 is forced against the correspondingly inclined surface 49 of the aperture in the carrying plate 3. That axial displacement is desirably imparted to the sleeve 1 by means of an insert 15, which is screw-threaded in the sleeve 1 and which in a modification of the embodiments shown in FIGS. 2 and 3 must be designed so that its end face 50 bears on the carrying plate 3.

In the embodiment shown in FIG. 2 the sleeve 1 is coupled with detent elements which consist of angularly spaced cams 9 and 10 provided on the end faces of two discs 11, 12. One of said discs 12 is held stationary and the second detent disc 11 is non-rotatably and axially displaceably connected to the sliding surface bearing and is under the influence of a resilient element, such as a rubber ring 13, which urges the axially diplaceable detent disc 11 toward the stationary detent disc 12. The stationary detent disc 12 may be connected to the carrying plate 3 by screws 51 or by an adhesive joint. The rubber ring 13 may be replaced by other reslient elements, e.g., by axially extending pins, which resiliently bear on the detent disc 11, or by disc springs disposed between the detent disc 11 and a stationary stop 8. The stop 8 engaged by the rubber ring 13 consists of a shoulder 14, which is formed by the insert 15 that can be screwed into the sleeve 1. The shoulder engages the sleeve 1 on that end face which is remote from the carrying plate 3.

In accordance with FIG. 3 the sliding surface bearing is coupled to friction elements. The friction element consists of a disc 5, which is non-rotatably connected to the sleeve 1 and with one end face engages a friction ring 6, which is non-rotatably connected to the carrying plate 3 for the artificial hand 4.

The friction disc 5 and the detent disc 11 are non-rotatably connected to the sleeve 1 by a tongue-and-groove joint, which permits of an axial displacement of said discs relative to the sleeve 1.

The friction disc 5 is axially displaceable by an adjusting nut 7, which is screwed on the friction disc 5 and bears on the stationary stop 8, which as in the embodiment shown in FIG. 2 is formed by the shoulder 14 of the insert 15, which is screwed in the sleeve 1.

The friction ring 6 is fitted on a centering collar 52 of the carrying plate 3 of the artificial hand 4.

Figure 5:
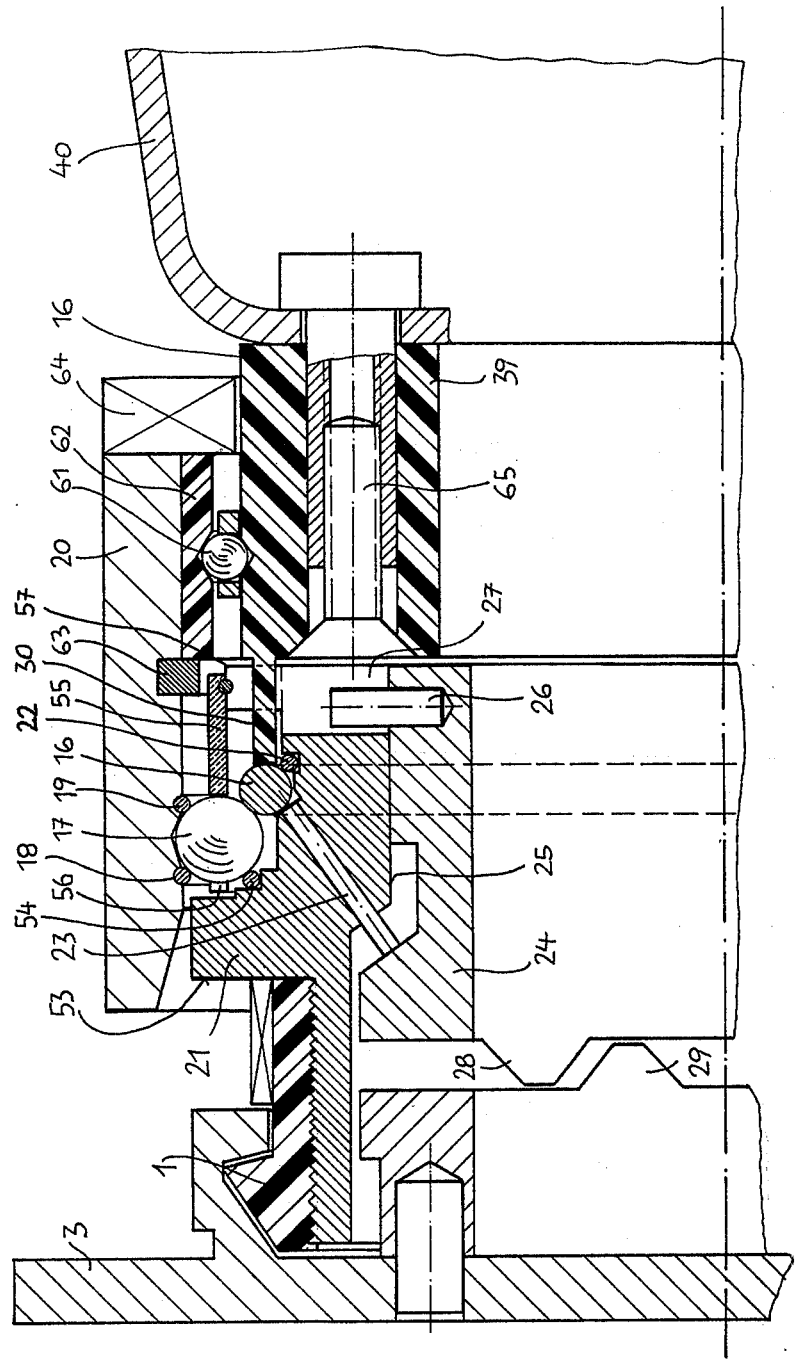
FIG. 5 shows an arrangement which is similar to that of FIG. 4 but enables an active pivotal or rotational movement of the artificial hand.

In the embodiments shown in FIGS. 4 and 5, the prosthesis shaft is connected to the artificial hand by a rolling element bearing, the rolling elements of which consist of balls 17, which by an adjusting mechanism are movable in a substantially radial direction into and out of engagement with a track, which is provided on a retaining member 20 that is connected to the prosthesis shaft 46. Alternatively, the track with which the rolling elements are engageable to connect the artificial hand 4 to the prosthesis shaft 46 may be provided on a retaining member which is connected to the artificial hand. The track for the rolling elements may be formed directly on the retaining member 20. In an alternative arrangement, shown in FIGS. 4 and 5, the track may be formed by two axially spaced apart wire rings 18, 19, which are held in annular grooves of the sleevelike member 20. The wire rings 18, 19 have abutting ends.

The balls 17 are mounted on a retaining member 21, which is connected to the artificial hand 4 and which like the insert 15 shown in FIGS. 2 and 3 is screw-threaded in the sleeve 1 and has a shoulder 53 which engages the sleeve 1 of the sliding surface bearing at the end face which is remote from the artificial hand 4. The sliding surface bearing is coupled to friction or detent elements which are not shown in FIGS. 4 and 5 and may be similar to those shown in FIGS. 2 and 3. The raceway for the balls 17 is provided on the retaining member 21 and is formed by two rings, which like the wire rings 18, 19 in the retaining member 20 consist of spring steel and have abutting ends. The two rings carried by the retaining member 21 form an axially displaceable backing ring 16 for the balls 17 and consist of wire which is larger in diameter than the wire rings 18, 19 in the retaining member 20 and the second wire ring 54 of the retaining member 21. The wire ring 54 has the same wire diameter as the wire rings 18 and 19. In the position shown in FIGS. 4 and 5, the backing ring 16 engages the balls 17 and holds the same in engagement with the wire rings 18, 19 carried by the retaining member 20 and forming a raceway for the balls 17. By these means the artificial hand 4 is connected to the prosthesis shaft 46. In that position the backing ring 16 engages a stationary stop of the retaining member 21 connected to the artificial hand 4. In the embodiment shown by way of example that stop is formed by a wire ring 22, which is held in an annular groove formed in the retaining member 21. When the backing ring 16 is axially displaced away from the balls 17 (to the right in FIGS. 4 and 5), the retaining ring moves over the wire ring 22 and is thus expanded in diameter so that the balls 17 have no longer an inner raceway and move inwardly to disengage the outer raceway formed by the wire rings 18, 19. The retaining member 20 connected to the prosthesis shaft 46 can now be axially pulled from the retaining member 21, which is connected to the artificial hand 4. The balls 17 are mounted in a cage 55, which consists, e.g., of plastic material and is provided with unilaterally open pockets 56 for receiving the balls 17. The cage 55 is held against an end flange 57 of the retaining member 21.

To enable an axial displacement of the retaining ring, the retaining member 21 is provided with, e.g., six bores, which extend at an acute angle of, e.g., 30° to the axis of the sleeve 1 and in which pins 23 are slidably guided, which at one end engage the backing ring 16 and at the other end bear on a bushing 24, which is axially displaceably mounted in a bore 25 of the retaining member 21. The bushing 24 has a bevelled surface 58 engaged by the pins 23. When the bushing 24 is axially displaced (to the right in FIGS. 4 and 5), the pins 23 move the backing ring 16 to the right, away from the balls 17. To enable an axial displacement of the bushing 24, the latter is provided with an axially projecting cam 28 on that end face which faces the artificial hand. The cam 28 cooperates with a second cam 29, which is preferably similar in shape to the cam 28 and is firmly connected to the artificial hand 4, particularly to the carrying plate 3 thereof. To prevent a rotation of the bushing 24, a radially protruding pin 26 is secured to the bushing and engages a groove 27, which is formed in the retaining member 21. Like the cam 28, the second cam 29 is formed on a bushing 58, which by means of pins 59 is secured to the carrying plate 3 for the artificial hand 4.

To return the retaining ring 16 to the position in which it engages the balls 17, substantially axially extending pins 30 are provided, which with their free ends engage the retaining ring 16 and which are movable in unison in the direction of the axis of the ball bearing. In the embodiments shown by way of example in FIGS. 4 and 5 the arrangement is such that the pins 30 can be axially moved away from or toward the retaining member 21 only in unison with the component 20 which is connected to the prosthesis shaft 46. The pins 30 extend preferably through apertures 60 in the end flange 57 of the retaining member 21. The walls of the apertures 60 extend preferably at an oblique angle to each other so that those webs of the end flange 57 which are disposed between the apertures 60 are trapezoidal when they are developed onto a straight line.

Figure 6:
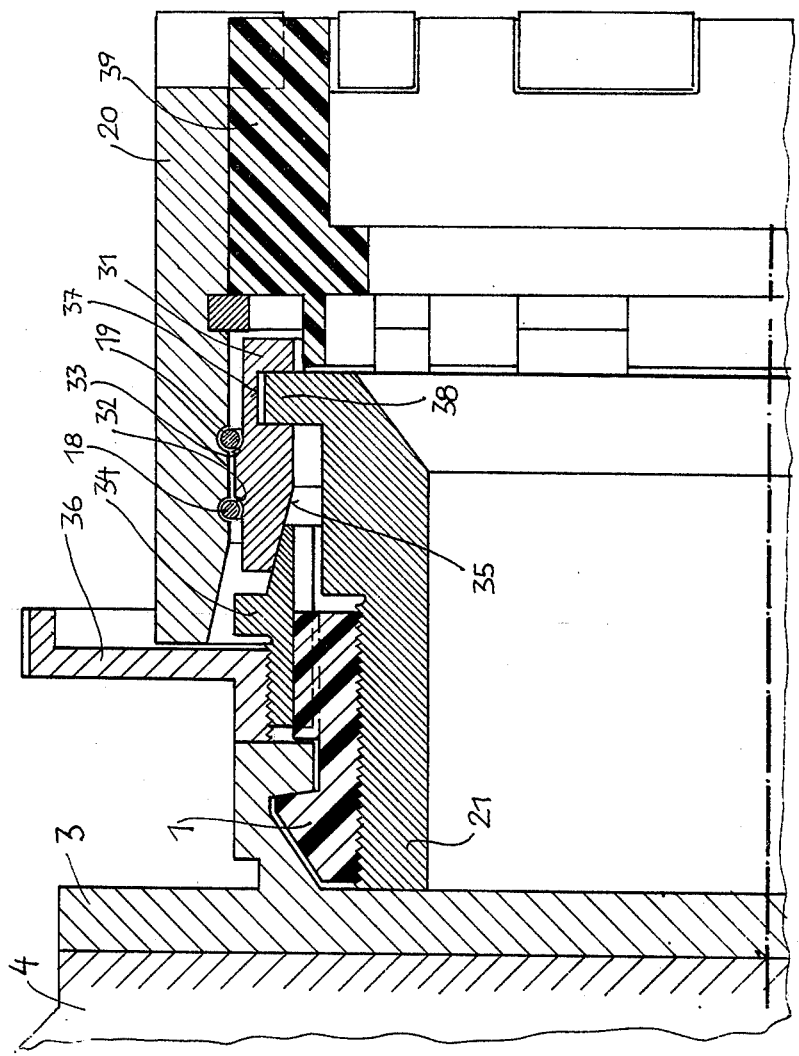
FIG. 6 shows a modification of the means shown in FIGS. 4 and 5 and serving to retain the artificial hand on the prosthesis shaft.

FIG. 6 shows an arrangement in which the prosthesis shaft 46 is connected to the artificial hand 4 by locking means which consist of a bushing 31, which is slitted throughout its length and which is formed on its outside peripheral surface with two shoulders 32, 33 which are spaced the same distance apart as the wire rings 18, 19. The bushing 31 consists preferably of plastics material and is expansible by an expanding mandrel 34, which is adapted to be introduced into the bushing 31 and slides on a conical inside surface 35 of the bushing 31. The expanding mandrel 34 is hollow, and the inside surface of the bore is formed with keyways, which receive tongues provided on the outside surface of the sleeve 1 which forms the sliding surface bearing. In this way, the expanding mandrel 34 is non-rotatably connected to the sleeve 1 but axially slidable relative thereto. For an axial displacement of the expanding mandrel 34, the latter is provided with external screw threads, which are engaged by an adjusting nut 36, which bears on the carrying plate 3 of the artificial hand 4.

An annular groove 37 provided in the inside surface of the bushing 31 receives a flange 38 of the retaining member 21 which is connected to the artificial hand and which is screw-threaded in the sleeve 1.

In the embodiment shown in FIGS. 4 and 5 and in that shown in FIG. 6, the retaining member 21 connected to the artificial hand 4 interengages with a coupling member 39, which is mounted in the retaining member 20 connected to the prosthesis shaft 46.

If the coupling member 39 is non-rotatably connected in the retaining member 20 connected to the prosthesis shaft (FIGS. 4 and 6) and a ball bearing is used, as shown in FIG. 4, the sleeve 1 is coupled to friction or detent elements because the bushings 58 and 24 must be rotated relative to each other to separate the connection between the artificial hand and the prosthesis shaft whereas when the retaining element consists of the slit bushing 31 the sleeve 1 is non-rotatably connected to the carrying plate 3.

The coupling member 39 may be rotatably mounted in the retaining member 20, for instance, in the arrangement shown in FIG. 5 for the embodiment comprising a ball bearing 17. Alternatively, the coupling member 39 may be rotatably mounted also when the prosthesis shaft is connected to the artificial hand 4 by a bushing 31 which can be expanded in diameter. The coupling member 39 according to FIG. 5 is provided on its outside surface with an annular groove, which forms a raceway for balls 61, which cooperate with an outer raceway formed in an insert 62. The latter is disposed between a split locking ring 63 and an inwardly protruding flange 64, which is formed on the retaining member 20 and formed with slots. In that case the coupling part 39 is firmly connected, e.g., by screws 65, to the end cap 40 of the prosthesis shaft. The end cap 40 is capable of a limited angular movement relative to the prosthesis shaft just as the hand can be pivotally moved although the flesh is held on the lower arm. Instead of deriving a rotational drive from the end cap 40, a separate drive motor may be provided for this purpose and may consist of an electric motor or a hydraulic or pneumatic fluid drive.

The pins 30 (FIGS. 4 and 5) for returning the retaining ring 16 to the position in which it engages the balls 17 desirably protrude from the end face of the coupling member 39.

The retaining member 20 to be connected to the prosthesis shaft 46 and/or the retaining member connected to the artificial hand 4 may be adapted to the desired peripheral extent and peripheral configuration of the hand by an application thereto of thermoplastic or thermosetting plastic material and/or of annular members consisting, e.g., of metal. In this case an artificial wrist may be provided which is designed for the smallest desired dimensions and can be modified to conform to the peripheral extent and configiration of any desired hand without need for a change of the elements of the artificial wrist.

In the embodiment shown in FIG. 7, the retaining member 20 to be connected to the prosthesis shaft 46 is provided with a spherical shell 41, which has a center M disposed on the axis of the sleevelike retaining member 20. To connect the spherical shell 41 to the retaining member 20, a flange ring 66 is fitted on and fixed to the retaining member 20. The spherical shell 41 is secured by screws 67 to the flange ring 66. Two clamping rings 44 and 45 are provided, which respectively engage the outside surface 42 and the inside surface 43, which is concentric thereto. The clamping rings 44, 45 are slidable relative to each other in the direction of their axis so that the spherical shell 41 can be secured in any desired position. The clamping ring 44 is slidably mounted on a collar 68 of the second clamping ring 45. An adjusting nut 69 is mounted on the clamping 45 and bears on the second clamping ring 44. An elastic ring 70 may be disposed between the nut 69 and the ring 44 if this is desired. The clamping rings 44, 45 consist preferably of metal and are provided with coverings 71, 72 of plastics material or the like in the areas in which they contact the spherical shell 41.

It is possible and also often desirable to use tubular structures of metal to connect the retaining member 20 to the prosthesis shaft which contacts the skin of the stump and to provide pieces of foamed plastics which simulate the shape of an arm. For this reason the system described here can be used also with upper arm prosthesis which have, e.g., a modular structure or comprise a tubular skeleton.

What is claimed is:

1. An artificial wrist for connecting an arm prosthesis shaft to an implement which comprises
   distal retaining means;
   a proximal retaining member adapted to extend into said prosthesis shaft and formed with first and second engaging surfaces;
   locking means interlocking with said distal retaining means and said first engaging surface to hold said distal retaining means and said proximal retaining member axially together;
   a sliding surface bearing adapted to rotatably connect an implement to said distal retaining means;
   rotatable coupling means which engage said second engaging surface and are adapted to engage said prosthesis shaft, said distal retaining means comprising a distal retaining member,
   one of said distal and proximal retaining member being provided a track which is engageable by said locking means,
   said locking means being carried by the other of said distal and proximal retaining members; and
   an adjusting mechanism operable to move said locking means in a substantially radial direction into and out of engagement with said track.

2. An artificial wrist as set forth in claim 1, in which said locking means comprise rolling elements,
   said proximal retaining member is provided with a raceway for said rolling elements.

3. An artificial wrist as set forth in claim 2, in which said rolling elements comprise balls.

4. An artificial wrist as set forth in claim 1, in which said locking means comprise a bushing, which engages said first engaging surface.

5. An artificial wrist as set forth in claim 1, in which a carrying plate is provided, which is adapted to be non-rotatably connected to said implement, and
   said sliding surface bearing comprises a sleeve, which has a portion which is hook-shaped in medial section and interengages with said carrying plate.

6. An artificial wrist as set forth in claim 1, which comprises friction means cooperating with said sliding surface bearing.

7. An artificial wrist as set forth in claim 6, in which said sliding surface bearing comprises a sleeve and said friction means comprise a friction disc non-rotatably connected to said sleeve.

8. An artificial wrist as set forth in claim 7, in which a carrying plate is provided, which is adapted to be non-rotatably connected to said implement, and
   said friction means comprise a friction ring, which is non-rotatably connected to said carrying plate and engages one end face of said friction disc.

9. An artificial wrist as set forth in claim 7, in which said friction disc is axially displaceable relative to said sleeve,
   a stop is axially fixed to said sleeve, and
   an adjusting nut is provided, which is screw-threaded on said friction disc and bears on said stop and is rotatable to impart an axial displacement to said friction disc.

10. An artificial wrist as set forth in claim 9, in which said friction disc is connected to said sleeve by a tongue-and-groove joint permitting of an axial displacement of the friction disc along said sleeve.

11. An artificial wrist as set forth in claim 9, in which an insert extends in and is screw-threadedly connected to said sleeve and formed with a shoulder, which constitutes said stop.

12. An artificial wrist as set forth in claim 1, which comprises detent means cooperating with said sliding surface bearing.

13. An artificial wrist as set forth in claim 12, in which
 a first disc is axially fixed to said sliding surface bearing,
 a second disc is non-rotatably connected to said sliding surface bearing and axially displaceable relative thereto,
 two angularly spaced detent cams are respectively provided on confronting end faces of said discs, and
 a resilient element is provided, which urges said second disc toward said first disc.

14. An artificial wrist as set forth in claim 13, in which said resilient element comprises a rubber ring.

15. An artificial wrist as set forth in claim 14, in which a stop is provided, which is axially fixed to said sliding surface bearing and engaged by said rubber ring.

16. An artificial wrist as set forth in claim 15, in which
 said sliding surface bearing comprises a sleeve, and
 an insert extends in and is screw-threadedly connected to said sleeve and formed with a shoulder, which constitutes said stop.

17. An artificial wrist as set forth in claim 1, in which
 said locking means comprise rolling elements engageable with said track and
 said adjusting mechanism is operable to move said rolling elements into and out of engagement with said track.

18. An artificial wrist as set forth in claim 17, in which
 said adjusting mechanism comprises a retaining ring which has a raceway and is axially displaceable relative to said rolling elements to and from a retaining position in which said rolling elements engage said raceway to hold said distal and proximal retaining members axially together.

19. An artificial wrist as set forth in claim 18, in which
 said retaining ring is a split ring,
 a stop ring is provided, which is engaged by said split ring in said retaining position and
 said retaining ring is expansible in diameter to be capable of axially moving away from said rolling elements past said stop.

20. An artificial wrist as set forth in claim 19, in which said stop consists of a wire ring.

21. An artificial wrist as set forth in claim 18, in which
 said retaining ring is fitted on said distal retaining member,
 said sliding surface bearing comprises a sleeve,
 said distal retaining member extends into said sleeve and is screw-threadedly connected thereto,
 said distal retaining member is provided with a plurality of bores, which extend at an acute angle to the axis of said sleeve,
 a plurality of pins are provided, each of which is slidable in one of said bores,
 said distal retaining member has a bore,
 a bushing is axially slidably mounted in said bore of said distal retaining member, and
 each of said pins engages at one end said retaining ring and at the other end said bushing.

22. An artificial wrist as set forth in claim 21, in which said bores extend at an angle of 30° to the axis of said sleeve.

23. An artificial wrist as set forth in claim 21, in which
 said bushing is non-rotatably connected to said distal retaining member and has a distal end face provided with an axially protruding first cam and
 an implement-connecting member is provided, which has a second cam adapted to cooperate with said first cam.

24. An artificial wrist as set forth in claim 23, in which
 said distal retaining member is formed with a groove and
 said bushing carries a pin which extends into said groove to non-rotatably connect said bushing to said distal retaining member.

25. An artificial wrist as set forth in claim 4, in which said first and second cams are similarly shaped.

26. An artificial wrist as set forth in claim 23, in which said implement-connecting member comprises a carrying plate.

27. An artificial wrist as set forth in claim 18, which comprises
 a plurality of substantially axially extending pins having free ends which engage said retaining ring,
 said pins being movable in unison in the axial direction of said track to move said retaining ring to said retaining position.

28. An artificial wrist as set forth in claim 27, in which
 said locking means are carried by said distal retaining member,
 a coupling member is mounted in said proximal retaining member and interengages with said distal retaining member, and
 said pins protrude from the end face of said coupling member.

29. An artificial wrist as set forth in claim 1, in which said track is formed by two axially spaced apart wire rings.

30. An artificial wrist as set forth in claim 29, in which
 said locking means comprise a bushing, which is slit throughout its length and has a conical inside peripheral surface and is formed on its outside peripheral surface with two shoulders spaced the same distance apart as said wire rings, and
 an expanding mandrel is provided, which is adapted to be inserted into said bushing and slidable along said conical peripheral surface to expand said bushing.

31. An artificial wrist as set forth in claim 30, in which
 said sliding surface bearing comprises a sleeve,
 said expanding mandrel is non-rotatably connected to said sleeve and axially slidable relative thereto and provided with external screw threads,
 a carrying plate is provided, which is adapted to carry said implement, and
 an adjusting nut engages said carrying plate and threadably engages said screw threads.

32. An artificial wrist as set forth in claim 31, in which
said sliding surface bearing consists of a sleeve,
said distal retaining member extends into said sleeve and is screw-threadedly connected thereto and formed with a flange, and
and bushing is formed on its inside surface with an annular groove, which receives said flange.

33. An artificial wrist as set forth in claim 1, in which
said locking means are carried by distal retaining member and
a coupling member is mounted in said proximal retaining member and interengages with said distal retaining member.

34. An artificial wrist as set forth in claim 33, in which
said coupling member is non-rotatably connected to said proximal retaining member.

35. An artificial wrist as set forth in claim 34, in which
said locking means comprise rolling elements,
said sliding surface bearing comprises a sleeve, and detent means are coupled to said sleeve.

36. An artificial wrist as set forth in claim 34, in which
said locking means comprise an expansible bushing, and
implement-connecting means are provided, which are non-rotatably connected to said sliding surface bearing.

37. An artificial wrist as set forth in claim 36, in which said sliding surface bearing comprises a sleeve, which is non-rotatably connected to said implement connecting means.

38. An artificial wrist as set forth in claim 36, in which said implement-connecting means comprise a carrying plate.

39. An artificial wrist as set forth in claim 28, in which
said coupling member is rotatably mounted in said proximal retaining member.

40. An artificial wrist as set forth in claim 21, in which at least one of said distal retaining means and proximal retaining members carries covering means having a desired peripheral extent and configuration.

41. An artificial wrist as set forth in claim 40, in which said covering means comprise synthetic thermoplastic material.

42. An artificial wrist as set forth in claim 40, in which said covering means comprise synthetic thermosetting material.

43. An artificial wrist as set forth in claim 40, in which said covering means comprise annular means.

44. An artificial wrist as set forth in claim 43, in which said annular means consist of metal.

45. An arm prosthesis, which comprises
an arm prosthesis shaft and
an artificial wrist for connecting said prothesis shaft to an implement, said artificial wrist comprising distal retaining means;
a proximal retaining member extending into said prosthesis shaft and formed with first and second engaging surfaces;
locking means interlocking with said distal retaining means and said first engaging surface to hold said distal retaining means and said proximal retaining member axially together;
a sliding surface bearing adapted to rotatably connect an implement to said distal retaining means;
rotatable coupling means which engage said second engaging surface and said prothesis shaft, said distal retaining means comprising a distal retaining member connected to said sliding surface bearing,
said proximal retaining member being provided with a track which is engageable by said locking means,
said locking means being carried by said distal retaining member;
an adjusting mechanism operable to move said locking means in a substantially radial direction into and out of engagement with said track; and
a coupling member rotatably mounted in said proximal retaining member and interengages with said distal retaining member.

46. An arm prosthesis as set forth in claim 45, in which an implement is rotatably connected by said sliding surface bearing to said distal retaining means.

47. An arm prosthesis as set forth in claim 46, in which said implement is an artificial hand.

48. An arm prosthesis as set forth in claim 46, in which said implement comprises a carrying plate connected to said sliding surface bearing.

49. An arm prosthesis as set forth in claim 45, in which
said prosthesis shaft carries an end cap, which is non-rotatably connected to said coupling member.

50. An arm prosthesis as set forth in claim 45, which comprises rotary drive means non-rotatably connected to said coupling member and operable to rotate the same.

51. An artificial wrist for connecting an arm prosthesis shaft to an implement, which comprises:
distal retaining means;
a proximal retaining member adapted to extend into said prosthesis shaft and formed with first and second engaging surfaces;
locking means interlocking with said distal retaining means and said first engaging surface to hold said distal retaining means and said proximal retaining member axially together, said locking means including rolling elements;
a sliding surface bearing adapted to rotatably connect an implement to said distal retaining means;
an adjusting mechanism operable to move said locking means in a substantially radial direction into and out of engagement with one of said distal retaining means and proximal retaining member;
rotatable coupling means which engage said second engaging surface and are adapted to engage said prosthesis shaft, said adjusting mechanism comprising a retaining ring which has a raceway and is axially displaceable relative to said rolling elements to and from a retaining position in which said rolling elements engage said raceway to hold said distal retaining means and proximal retaining member axially together; and
a plurality of substantially axially extending pins having free ends which engage said retaining ring, said pins being movable in unison in the axial direction of said track to move said retaining ring to said retaining position.

52. An artificial wrist as set forth in claim 51, in which said locking means are carried by said distal retaining means,
a coupling member is mounted in said proximal retaining member and interengages with said distal retaining means, and said pins protrude from the end face of said coupling member.

* * * * *

UNITED STATES PATENT AND TRADEMARK OFFICE
CERTIFICATE OF CORRECTION

PATENT NO. : 4,010,495
DATED : 8 March 1977
INVENTOR(S) : Eduard HORVATH

It is certified that error appears in the above-identified patent and that said Letters Patent are hereby corrected as shown below:

In the heading, line /73/ read the assignee as follows:

-- Otto Bock Orthopädische Industrie KG, Duderstadt, Germany -- .

Signed and Sealed this twelfth Day of July 1977

[SEAL]

Attest:

RUTH C. MASON
Attesting Officer

C. MARSHALL DANN
Commissioner of Patents and Trademarks